United States Patent
Suzuki

(10) Patent No.: US 9,868,681 B2
(45) Date of Patent: Jan. 16, 2018

(54) PRODUCTION METHOD FOR γ,δ-UNSATURATED ALCOHOLS

(71) Applicant: KURARAY CO., LTD., Kurashiki-shi (JP)

(72) Inventor: Yutaka Suzuki, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/312,936

(22) PCT Filed: Jun. 2, 2015

(86) PCT No.: PCT/JP2015/065891
§ 371 (c)(1),
(2) Date: Nov. 21, 2016

(87) PCT Pub. No.: WO2015/186699
PCT Pub. Date: Dec. 10, 2015

(65) Prior Publication Data
US 2017/0197895 A1    Jul. 13, 2017

(30) Foreign Application Priority Data
Jun. 2, 2014   (JP) .................................. 2014-113960

(51) Int. Cl.
*C07C 29/44* (2006.01)
*C07C 29/80* (2006.01)

(52) U.S. Cl.
CPC .............. *C07C 29/44* (2013.01); *C07C 29/80* (2013.01)

(58) Field of Classification Search
CPC ................................ C07C 29/44; C07C 29/80
See application file for complete search history.

(56) References Cited

U.S. PATENT DOCUMENTS 2,335,027 A   11/1943  Ritter

FOREIGN PATENT DOCUMENTS

| JP | 47-47362 B | 11/1972 |
| JP | 47-51322 B | 12/1972 |
| JP | 7-285899 A | 10/1995 |
| WO | 02/051776 A2 | 7/2002 |

OTHER PUBLICATIONS

Jp 07285899 machine translation, 10, 1995.*
International Search Report dated Sep. 1, 2015, in PCT/JP2015/065891, filed Jun. 2, 2015.
Brace, Neal O., "The Uncatalyzed Thermal Addition of Formaldehyde to Olefins", Journal of the American Chemical Society, vol. 77, Iss. 17, Sep. 5, 1955, pp. 4666-4668.

* cited by examiner

*Primary Examiner* — Jafar Parsa
(74) *Attorney, Agent, or Firm* — Oblon, McClelland, Maier & Neustadt, L.L.P.

(57) ABSTRACT

Provided is a method from which a γ,δ-unsaturated alcohol having a much more smaller amount of inclusion of formic acid and a formic acid ester and having a high purity can be obtained in a high yield. Specifically, provided is a method for producing a γ,δ-unsaturated alcohol by causing a reaction between an α-olefin and formaldehyde, the method including a step of bringing a reaction liquid obtained through the reaction into contact with an alkaline aqueous solution so as to provide an aqueous solution having pH of 9 to 13.

12 Claims, No Drawings

PRODUCTION METHOD FOR γ,δ-UNSATURATED ALCOHOLS

TECHNICAL FIELD

The present invention relates to a method for producing a γ,δ-unsaturated alcohol.

BACKGROUND ART

A γ,δ-unsaturated alcohol has a double bond and a hydroxyl group in a molecule thereof, and by converting the respective functional groups, it can be converted into a variety of organic compounds. Therefore, the γ,δ-unsaturated alcohol is an extremely useful compound in the field of organic synthetic chemistry.

As one of production methods of the foregoing γ,δ-unsaturated alcohol, there is known a method of subjecting an α-olefin of every sort and kind and an aldehyde to thermal reaction in the absence of a catalyst. For example, PTL 1 and NPL 1 disclose a method of allowing an α-olefin and an aldehyde to react with each other at 100 to 250° C. for 2 to 16 hours under a high pressure of 200 atm (20 MPa) or more.

A problem of this reaction resides in the matter that the formation of an acid is caused due to disproportionation of an aldehyde (see PTL 2), namely in the case of using formaldehyde, formic acid is formed. The acid, such as formic acid, not only causes corrosion of an apparatus but also reacts with a γ,δ-unsaturated alcohol to form an ester during the reaction or purification, thereby decreasing the yield of the γ,δ-unsaturated alcohol. Furthermore, the foregoing ester is included into the γ,δ-unsaturated alcohol at the time of purification by distillation, thereby causing deterioration of purity or quality of products.

As a method of solving the aforementioned problem, PTLs 2 and 3 recommend a method of carrying out the aforementioned reaction in the presence of a basic compound, such as ammonia, hexamethylenetetramine, etc. In PTL 4, an α-olefin and an aldehyde are allowed to react with each other using a phosphate as the basic compound at −20 to 320° C. and at 100 to 250 atm (10 to 25 MPa), whereby a γ,δ-unsaturated alcohol is obtained in a relatively good yield. But, the methods of PTLs 2 to 4 involve such a problem that in the case of performing the reaction in the absence of a basic compound, a thorough industrial yield is not obtained. In addition, in the case of using a nitrogen-containing compound as the basic compound, there is involved such a problem that a minute amount of the decomposed nitrogen-containing compound is included into a product. In addition, in the method using a phosphate as in PTL 4, though no inclusion of the phosphate into a product occurs, there is caused such a fault that the phosphate with low solubility is deposited in a reactor or a piping, thereby causing clogging of the piping.

Then, PTL 5 discloses that taking the aforementioned problem of PTL 3, in a method of carrying out the reaction of an α-olefin and formaldehyde in the presence of a solvent at 150 to 350° C. and at 30 to 500 atm (3 to 50 MPa), by adopting an alcohol having 3 to 10 carbon atoms as a solvent and using the solvent in an amount of 2 to 20 molar times to formaldehyde in a formalin aqueous solution, even if the reaction is performed in the absence of a basic compound, the formation of a by-product can be inhibited. According to the foregoing method, a product is obtained in a selectivity of about 91% at maximum.

CITATION LIST

Patent Literature

PTL 1: U.S. Pat. No. 2,335,027
PTL 2: JP 47-51322 B
PTL 3: JP 47-47362 B
PTL 4: WO 02/051776 A
PTL 5: JP 7-285899 A

Non-Patent Literature

NPL 1: *Journal of the American Chemical Society* (*J. Am. Chem. Soc.*), Vol. 77, p.4666, 1955

SUMMARY OF INVENTION

Technical Problem

But, the present inventor further investigated the method described in PTL 5. As a result, it has become clear that the by-production amount of formic acid does not become substantially zero, and the foregoing formic acid not only causes corrosion of an apparatus but also reacts with the γ,δ-unsaturated alcohol during the reaction or purification to form an ester, so that the problem of decreasing the yield of the γ,δ-unsaturated alcohol still remains. At the same time, it has become clear that there is room for more improvements in the purity and yield of the obtained γ,δ-unsaturated alcohol.

Thus, a problem of the present invention is to provide a method from which a γ,δ-unsaturated alcohol having a much more smaller amount of inclusion of formic acid and a formic acid ester and having a high purity can be obtained in a high yield.

Solution To Problem

The present inventor made extensive and intensive investigations regarding a production method of a γ,δ-unsaturated alcohol. As a result, it has been found that even in a reaction liquid obtained by performing reaction without using a basic compound, when pH of an aqueous solution that is obtained by bringing it into contact with an alkaline aqueous solution is regulated to 9 to 13, preferably 10 to 13, more preferably 11 to 13, and still more preferably 12 to 13, all of formic acid and a formic acid ester are converted into a formate and removed, whereby the purity of the target material is increased; and at the same time, a γ,δ-unsaturated alcohol is formed from an ester moiety of the formic acid ester, whereby the yield of the target material is increased, leading to accomplishment of the present invention.

The present invention is concerned with the following [1] to [9].

[1] A method for producing a γ,δ-unsaturated alcohol represented by the following general formula (II);

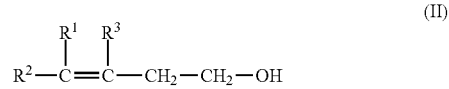

(II)

wherein $R^1$, $R^2$, and $R^3$ each independently represent a hydrogen atom, an optionally hydroxyl group-substituted alkyl group having 1 to 10 carbon atoms, an optionally hydroxyl group-substituted alkenyl group having 2 to 10 carbon atoms, or an optionally hydroxyl group-substituted aryl group having 6 to 12 carbon atoms, provided that $R^1$ and $R^3$ may be bonded to each other to form a ring, the method including:

a step of causing a reaction between an α-olefin represented by the following general formula (I):

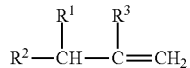
(I)

wherein $R^1$, $R^2$, and $R^3$ are the same as defined above, and formaldehyde, and a step of bringing a reaction liquid obtained through the reaction into contact with an alkaline aqueous solution so as to provide an aqueous solution having pH of 9 to 13.

[2] The method for producing a γ,δ-unsaturated alcohol as set forth above in [1], wherein an alkali in the alkaline aqueous solution is at least one selected from an alkali metal hydroxide, an alkali metal carbonate, an alkali metal acetate, an alkali metal phosphate, an alkaline earth metal hydroxide, an alkaline earth metal carbonate, an alkaline earth metal acetate, and an alkaline earth metal phosphate.

[3] The method for producing a γ,δ-unsaturated alcohol as set forth above in [1] or [2], wherein a concentration of the alkali in the alkaline aqueous solution is 0.01 to 20 mol/L.

[4] The method for producing a γ,δ-unsaturated alcohol as set forth above in any one of [1] to [3], wherein a temperature on the occasion of bringing the reaction liquid into contact with the alkaline aqueous solution is 10 to 90° C.

[5] The method for producing a γ,δ-unsaturated alcohol as set forth above in any one of [1] to [4], wherein the contact between the reaction liquid and the alkaline aqueous solution is performed in a counter-current mode.

[6] The method for producing a γ,δ-unsaturated alcohol as set forth above in any one of [1] to [5], wherein after bringing the reaction liquid into contact with the alkaline aqueous solution, purification by distillation is performed.

[7] The method for producing a γ,δ-unsaturated alcohol as set forth above in any one of [1] to [6], wherein $R^3$ is an alkyl group having 1 to 5 carbon atoms.

[8] The method for producing a γ,δ-unsaturated alcohol as set forth above in any one of [1] to [7], wherein at least one of $R^1$ and $R^2$ is a hydrogen atom.

[9] The method for producing a γ,δ-unsaturated alcohol as set forth above in any one of [1] to [8], wherein the reaction is performed in the presence of a solvent being in an amount of 0.5 to 20 mol per mol of formaldehyde.

Advantageous Effects of Invention

In accordance with the present invention, a γ,δ-unsaturated alcohol having a much more smaller amount of inclusion of formic acid and a formic acid ester and having a high purity is obtained in a high yield.

DESCRIPTION OF EMBODIMENTS

In the present specification, the restrictive wording with "being preferred" can be arbitrarily selected, and a combination of restrictive wordings with "being preferred" may be said to be more preferred.

The present invention is concerned with a method for producing a γ,δ-unsaturated alcohol represented by the following general formula (II):

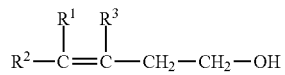
(II)

wherein $R^1$, $R^2$, and $R^3$ each independently represent a hydrogen atom, an optionally hydroxyl group-substituted alkyl group having 1 to 10 carbon atoms, an optionally hydroxyl group-substituted alkenyl group having 2 to 10 carbon atoms, or an optionally hydroxyl group-substituted aryl group having 6 to 12 carbon atoms, provided that $R^1$ and $R^2$ may be bonded to each other to form a ring, the method including a step of causing a reaction between an α-olefin represented by the following general formula (I) [the α-olefin will be hereinafter referred to as "α-olefin (I)"]:

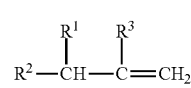
(I)

wherein $R^1$, $R^2$, and $R^3$ are the same as defined above, and formaldehyde, and a step of bringing a reaction liquid obtained through the reaction into contact with an alkaline aqueous solution (this operation will be hereinafter sometimes referred to as "alkali cleaning") so as to provide an aqueous solution having pH of 9 to 13, preferably 10 to 13, more preferably 11 to 13, and still more preferably 12 to 13.

(α-Olefin (I))

In the α-olefin (I) represented by the general formula (I), that is one of the raw materials, $R^1$, $R^2$, and $R^3$ each independently represent a hydrogen atom, an optionally hydroxyl group-substituted alkyl group having 1 to 10 carbon atoms, an optionally hydroxyl group-substituted alkenyl group having 2 to 10 carbon atoms, or an optionally hydroxyl group-substituted aryl group having 6 to 12 carbon atoms, provided that $R^1$ and $R^3$ may be bonded to each other to form a ring.

Examples of the aforementioned alkyl group having 1 to 10 carbon atoms include a methyl group, an ethyl group, various propyl groups (the term "various" expresses that a straight-chain group and every branched-chain group are included; hereinafter the same), various butyl groups, various hexyl groups, various octyl groups, various decyl groups, and the like. Above all, an alkyl group having 1 to 6 carbon atoms is preferred, an alkyl group having 1 to 3 carbon atoms is more preferred, and a methyl group is still more preferred. As the hydroxyl group-substituted alkyl group having 1 to 10 carbon atoms, it is not particularly limited so long as it is one in which a hydroxyl group is substituted on the aforementioned alkyl group having 1 to 10 carbon atoms, and the number of the hydroxyl group is preferably 1 to 3, and more preferably 1. Examples of the hydroxyl group-substituted alkyl group having 1 to 10 carbon atoms include a methylol group, a 2-hydroxyethyl group, a 4-hydroxy-n-butyl group, and the like. The carbon number of the hydroxyl group-substituted alkyl group having 1 to 10 carbon atoms is preferably 1 to 6, more preferably 1 to 3, and still more preferably 1.

Examples of the aforementioned alkenyl group having 2 to 10 carbon atoms include a vinyl group, an allyl group, an isopropenyl group, a 5-hexen-1-yl group, a 3-hexen-1-yl group, a 7-octen-1-yl group, a 5-octen-1-yl group, a 9-decen-1-yl group, a 7-decen-1-yl group, and the like. Above all, an alkenyl group having 2 to 6 carbon atoms is preferred, and an alkenyl group having 2 to 4 carbon atoms is more preferred. As the hydroxyl group-substituted alkenyl group having 2 to 10 carbon atoms, it is not particularly limited so long as it is one in which a hydroxyl group is substituted on the aforementioned alkenyl group having 2 to 10 carbon atoms, and the number of the hydroxyl group is preferably 1 to 3, and more preferably 1. Examples of the hydroxyl group-substituted alkenyl group having 2 to 10 carbon atoms include a 2-hydroxy-5-hexen-1-yl group, a 2-hydroxy-5-octen-1-yl group, and the like. The carbon number of the hydroxyl group-substituted alkenyl group having 2 to 10 carbon atoms is preferably 3 to 10, more preferably 3 to 6, and still more preferably 3 to 4.

Examples of the aforementioned aryl group having 6 to 12 carbon atoms include a phenyl group, a naphthyl group, and a biphenylyl group. Above all, an aryl group having 6 to 10 carbon atoms is preferred. As the hydroxyl group-substituted aryl group having 6 to 12 carbon atoms, it is not particularly limited so long as it is one in which a hydroxyl group is substituted on the aforementioned aryl group having 6 to 12 carbon atoms, and the number of the hydroxyl group is preferably 1 to 3, and more preferably 1. Examples of the hydroxyl group-substituted aryl group having 6 to 12 carbon atoms include a 2-hydroxyphenyl group, a 3-hydroxyphenyl group, a 4-hydroxyphenyl group, a 2-hydroxy-1-naphthyl group, a 3-hydroxy-1-naphthyl group, a 4-hydroxy-1-naphthyl group, an 8-hydroxy-1-naphthyl group, a 1-hydroxy-2-naphthyl group, and the like. The carbon number of the hydroxy group-substituted aryl group having 6 to 12 carbon atoms is preferably 6 to 10.

As the ring in the case where $R^1$ and $R^3$ are bonded to each other to form a ring, in the general formula (I), a saturated aliphatic ring having 5 to 10 carbon atoms, such as cyclopentane (5-membered ring), cyclohexane (6-membered ring), cyclooctane (8-membered ring), is preferably exemplified. Above all, the ring is preferably cyclohexane (6-membered ring). In the general formula (II), a ring having 5 to 10 carbon atoms, such as cyclopentene (5-membered ring), cyclohexene (6-membered ring), cyclooctene (8-membered ring), is exemplified.

Of those, from the viewpoint of decreasing a by-product, $R^3$ is preferably an alkyl group having 1 to 10 carbon atoms, and more preferably an alkyl group having 1 to 5 carbon atoms. In addition, it is preferred that at least one of $R^1$ and $R^2$ is a hydrogen atom. It is more preferred that at least one of $R^1$ and $R^2$ is a hydrogen atom, and $R^3$ is an alkyl group having 1 to 10 carbon atoms (still more preferably an alkyl group having 1 to 5 carbon atoms). It is especially preferred that all of $R^1$ and $R^2$ are a hydrogen atom, and $R^3$ is an alkyl group having 1 to 10 carbon atoms. More preferred examples of the respective groups are the same as described above.

Specific examples of a combination of $R^1$, $R^2$, and $R^3$ include (1) a combination in which all of $R^1$, $R^2$, and $R^3$ are a hydrogen atom [α-olefin (I)=propylene], (2) a combination in which $R^1$ and $R^2$ are a hydrogen atom, and $R^3$ is an alkyl group having 1 to 10 carbon atom [for example, α-olefin (I)=isobutene ($R^3$ is a methyl group), etc.], (3) a combination in which at least one of $R^1$ and $R^2$ is a hydrogen atom (preferably the other is an alkyl group having 1 to 10 carbon atoms), and $R^3$ is an alkyl group having 1 to 10 carbon atoms [for example, α-olefin (I)=2-methyl-1-butene, 2-methyl-1-pentene, 2-methyl-1-hexene, 2-methyl-1-heptene, 2-methyl-1-octene, etc.], (4) a combination in which all of $R^1$, $R^2$, and $R^3$ are an alkyl group having 1 to 10 carbon atoms [for example, α-olefin (I)=2,3-dimethyl-1-butene, etc.], (5) a combination in which $R^1$ and $R^2$ are a hydrogen atom, and $R^3$ is an aryl group having 6 to 10 carbon atoms [for example, α-olefin (I)=α-methylstyrene, etc.], (6) a combination in which $R^2$ is a hydrogen atom, and $R^1$ and $R^3$ are bonded to each other to form a ring [for example, α-olefin (I)=methylenecyclohexane, etc.], (7) a combination in which one of $R^1$ and $R^2$ is a hydrogen atom, the other being a hydroxyl group-substituted alkyl group having 1 to 10 carbon atoms, and $R^3$ is a hydrogen atom [for example, α-olefin (I)=3-buten-1-ol, etc.], (8) a combination in which one of $R^1$ and $R^2$ is a hydrogen atom, the other being a hydroxyl group-substituted alkyl group having 1 to 10 carbon atoms, and $R^3$ is an alkyl group having 1 to 10 carbon atoms [for example, α-olefin (I)=3-methyl-3-buten-1-ol, etc.], and the like.

In the case where at least one of $R^1$, $R^2$, and $R^3$ represents an alkenyl group or an aryl group, there might be a case where a material resulting from reaction of the alkenyl group or aryl group with formaldehyde is formed.

The amount of the α-olefin (I) used is preferably 1 to 50 mol, more preferably 3 to 30 mol, and still more preferably 3 to 15 mol per mol of formaldehyde. When the amount of the α-olefin (I) used is 1 mol or more per mol of formaldehyde, the selectivity of the target γ,δ-unsaturated alcohol is improved; whereas when it is 50 mol or less, equipment required for recovery of the α-olefin (I) becomes small, so that not only the industrial value is improved, but also there is a tendency that the volumetric efficiency is improved, and the productivity is improved.

(Formaldehyde)

Though formaldehyde may be used as it is, one having been dissolved in a solvent can also be used. Though the solvent that dissolves formaldehyde therein is not particularly limited, it is preferably water from the standpoint of easy availability, namely it is preferred to use a formaldehyde aqueous solution (formalin). In addition, from the viewpoint of volumetric efficiency, it is preferred that the concentration of formaldehyde is higher. However, when the concentration of formaldehyde is too high, a problem of deposition is caused, resulting in making its handling difficult. Thus, the concentration of the formaldehyde solution is preferably 10 to 70 mass %, and more preferably 30 to 60 mass %.

(Solvent)

The present reaction can be carried out in the presence or absence of a solvent. The solvent is not particularly limited so long as it does not adversely affect the reaction. Preferably, examples of the solvent include organic solvents, for example, aliphatic hydrocarbons, such as pentane, hexane, heptane, octane, nonane, decane, cyclohexane, cyclooctane, aromatic hydrocarbons, such as benzene, toluene, xylene, mesitylene, alcohols, such as, methanol, ethanol, tert-butanol, ethers, such as diethyl ether, diisopropyl ether, tetrahydrofuran, and the like.

Above all, alcohols are preferred, and alcohols having 3 to 10 carbon atoms are more preferred. Examples of the alcohol having 3 to 10 carbon atoms include aliphatic alcohols, such as n-propanol, isopropanol, n-butanol, tert-butanol, isobutanol, sec-butanol, n-amyl alcohol, isoamyl alcohol, tert-amyl alcohol, hexanol, 2-methyl-2-butanol, 3-methyl-3-pentanol, 2-ethylhexanol, heptanol, octanol, nonanol, alicyclic alcohols, such as cyclohexanol, methylcyclohexanol, cyclopentanol, aromatic alcohols, such as benzyl alcohol, and the like. However, the alcohol is not limited thereto.

The solvent may be used alone or may be used in combination of two or more thereof. In addition, the solvent may be used in combination with other solvent so long as the present reaction is not adversely affected. As the solvent that dissolves uniformly the α-olefin and formaldehyde, among the alcohols having 3 to 10 carbon atoms, isopropanol, isobutanol, sec-butanol, tert-butanol, isoamyl alcohol, tert-amyl alcohol, and the like are preferred, with tert-butanol being more preferred.

The present reaction is preferably performed in the presence of the solvent being in an amount of preferably 0.5 to 20 mol, and more preferably 1 to 10 mol per mol of formaldehyde. When the amount of the solvent used is 0.5 mol or more per mol of formaldehyde, by-production of an alkyl-m-dioxane can be inhibited; whereas when it is 20 mol or less, the scale of distillation equipment required for performing separation and recovery and the use amount of steam and electric power as a heat source can be simplified, so that there is a tendency that the industrial value can be improved.

(Reaction Conditions, Etc.)

The reaction temperature is preferably 150 to 350° C., more preferably 200 to 330° C., and still more preferably 240 to 330° C. When the reaction temperature is 150° C. or higher, the reaction rate is large, and the reaction time can be shortened; whereas when it is 350° C. or lower, the decomposition reaction of formaldehyde and the formed γ,δ-unsaturated alcohol is suppressed, so that there is a tendency that a decrease of the yield of the target γ,δ-unsaturated alcohol can be suppressed.

The reaction time is properly determined according to the reaction temperature, and the reaction is completed for one minute to 30 minutes. Accordingly, even in the case of performing the reaction in a continuous mode as described later, a residence time within the reaction tube may be enough to be one minute to 30 minutes.

The reaction pressure is set to a vapor pressure of the α-olefin (I) at the reaction temperature or higher. In the case of using the α-olefin (I) exceeding critical conditions at a predetermined temperature, it is recommended to control the pressure as occasion demands. The reaction pressure is 3 to 50 MPa, more preferably 3 to 30 MPa, still more preferably 5 to 30 MPa, and especially preferably 10 to 30 MPa.

When the reaction pressure is a vapor pressure of the α-olefin (I) at a predetermined temperature or higher, the concentration of the α-olefin (I) in the reaction liquid becomes high, thereby brining an improvement in the selectivity of the γ,δ-unsaturated alcohol, and as the reaction pressure is higher, there is a tendency that the reaction rate and the selectivity of the γ,δ-unsaturated alcohol are improved. In addition, when the reaction pressure is controlled to 50 MPa or lower, the construction costs of pressure equipment are suppressed, and there is a tendency that a risk of rupture of the reaction apparatus is lowered, too.

For the reaction, it is preferred to use a reactor capable of controlling the aforementioned reaction temperature, reaction time, and reaction pressure. In addition, the reaction can be carried out by any method of a batch mode, a semi-batch mode, a continuous mode, and the like. It is preferred to perform the reaction in a continuous mode in which the conversion of formaldehyde becomes high, and the selectivity and yield of the γ,δ-unsaturated alcohol become high.

In the case of performing the reaction in a continuous mode, a specific and preferred embodiment is as follows. That is, a mixed solution containing the α-olefin (I), the formaldehyde aqueous solution, and the organic solvent in predetermined ratios is fed into a reaction tube heated at a predetermined temperature at a desired flow rate. The reaction pressure is regulated such that an outlet of a cooling tube connected to an outlet of the reaction tube is kept at a predetermined pressure, the aforementioned mixed solution is allowed to stay within the reaction tube for a predetermined time, and the reaction is performed while flowing out the reaction liquid from the outlet of the reaction tube. In the case where the α-olefin (I) remains in the obtained reaction liquid, it is preferred to aliquot the α-olefin (I) and again use it as the raw material.

(Alkali Cleaning Step)

The present invention includes a step (alkali cleaning step) of bringing the reaction liquid that is obtained through the aforementioned reaction into contact with an alkaline aqueous solution (performing alkali cleaning), such that pH of the aqueous solution obtained by bringing the both into contact with each other (that is, a mixed solution of water in the reaction liquid and the alkaline aqueous solution) is regulated to 9 to 13, preferably 10 to 13, more preferably 11 to 13, and still more preferably 12 to 13.

According to the foregoing step, the removal of formic acid and a formic acid ester and the improvement in yield of the γ,δ-unsaturated alcohol can be attained at the same time. This may be conjectured to be caused due to the following matter. That is, all of formic acid and the formic acid ester in the obtained reaction liquid are converted into a formate and removed, whereby the purity of the γ,δ-unsaturated alcohol increases, and at the same time, since the formic acid ester in the reaction liquid is a condensate of formic acid and the γ,δ-unsaturated alcohol, the γ,δ-unsaturated alcohol that is the target material is formed through decomposition. It has become clear that because of the presence of formic acid on the occasion of purification by distillation, the γ,δ-unsaturated alcohol is readily converted into a high-boiling compound; and that it is difficult to separate the formic acid ester from the γ,δ-unsaturated alcohol through distillation. Thus, meaning of the fact that the amount of inclusion of formic acid and the formic acid ester can be thoroughly decreased in the present alkali cleaning step is significant.

The method of bringing the reaction liquid into contact with the alkaline aqueous solution is not particularly limited. For example, (i) a method of introducing the reaction liquid and the alkaline aqueous solution into a stirring device-equipped vessel and stirring the both [batch mode]; (ii) a method of brining the reaction liquid and the alkaline aqueous solution into continuous contact with each other within a tower in a counter-current mode (preferably a complete counter-current mode) [continuous mode]; and the like can be adopted. Above all, from the viewpoint of efficiently performing the alkali cleaning, the method (ii) is preferred.

As the alkali, it is preferred to use at least one selected from an alkali metal hydroxide, an alkali metal carbonate, an alkali metal acetate, an alkali metal phosphate, an alkaline earth metal hydroxide, an alkaline earth metal carbonate, an alkaline earth metal acetate, and an alkaline earth metal phosphate. Above all, from the viewpoints of easy availability, removal efficiency of formic acid and the formic acid ester, and selectivity and yield of the γ,δ-unsaturated alcohol, sodium hydroxide, potassium hydroxide, sodium carbonate, and potassium carbonate are preferred, with sodium hydroxide being more preferred.

The alkali may be used alone or may be used in combination of two or more thereof.

In the present alkali cleaning step, from the viewpoints of removal efficiency of formic acid and the formic acid ester and selectivity and yield of the γ,δ-unsaturated alcohol, the "aqueous solution" of the alkali is used. Though the concentration of the alkali in the alkaline aqueous solution is not particularly limited, from the viewpoint of easy handling and also from the viewpoints of removal efficiency of formic acid and the formic acid ester and selectivity and yield of the γ,δ-unsaturated alcohol, it is preferably 0.01 to 20 mol/L, more preferably 0.1 to 20 mol/L, still more preferably 0.1 to 10 mol/L, and especially preferably 0.1 to 5 mol/L. By bringing such an alkaline aqueous solution into contact with the aforementioned reaction liquid, the pH of the aqueous solution in the obtained solution is regulated to 9 to 13, preferably 10 to 13, more preferably 11 to 13, and more preferably 12 to 13. In the light of the above, from the viewpoints of removal efficiency of formic acid and the formic acid ester and selectivity and yield of the γ,δ-unsaturated alcohol, pH of lower than 9 is insufficient as the pH of the aqueous solution in the solution obtained by bringing the alkaline aqueous solution and the aforementioned reaction liquid into contact with each other, and it is required that the foregoing aqueous solution exhibits an alkalinity stronger than that.

Though the temperature on the occasion of bringing the reaction liquid obtained through the aforementioned reaction and the alkaline aqueous solution into contact with each other is not particularly limited, from the viewpoints of removal efficiency of formic acid and the formic acid ester and selectivity and yield of the γ,δ-unsaturated alcohol, it is preferably 10 to 90° C., more preferably 20 to 90° C., still more preferably 35 to 85° C., and especially preferably 50 to 80° C.

As for the contact time between the reaction liquid obtained through the reaction and the alkaline aqueous solution, though any length may be adopted so long as the acid in the raw material liquid and the ester derived from the acid are thoroughly removed, it is preferably 2 minutes to 600 minutes, more preferably 5 minutes to 500 minutes, and still more preferably 30 minutes to 500 minutes. In the case of adopting the aforementioned complete counter-current mode, though strict consideration regarding the contact time is not necessary, it is preferred to regulate the contact such that the time for which the reaction liquid obtained through the reaction and the alkaline aqueous solution remain within the tower is 2 minutes to 600 minutes (preferably 5 minutes to 500 minutes, and more preferably 30 minutes to 500 minutes).

In the reaction liquid having gone through the alkali cleaning step, the content of formic acid that is an impurity is extremely small (0.01 mas % or less, and substantially 0 mass %), and therefore, there is no anxiety of corrosion of the apparatus by formic acid, and there is no concern that on the occasion of performing purification by distillation, the γ,δ-unsaturated alcohol is converted into a high-boiling compound due to formic acid, so that the yield can be maintained high.

(Purification Step)

In view of the fact that after going through the aforementioned alkali cleaning step, the resultant goes through a purification step, the γ,δ-unsaturated alcohol with a higher purity is obtained.

The purification method is not particularly limited, and after aliquoting an organic layer, the resultant may be purified by means of column chromatography or the like. However, in the case of continuously carrying out the purification on an industrial scale, purification by distillation is preferred. In the case of performing the purification by distillation, the number of theoretical plate of the distillation tower is preferably 10 to 60, more preferably 10 to 40, and still more preferably 10 to 30. In addition, a reflux ratio is preferably 0.5 to 1.5, and more preferably 0.7 to 1.2. Though the heating temperature and pressure on the occasion of performing the purification by distillation are not particularly limited, for example, the purification by distillation is preferably performed at 100 to 180° C. and at 3 to 10 kPa, and more preferably performed at 120 to 160° C. and at 3 to 7 kPa.

With respect to the purification by distillation, a high-purity γ,δ-unsaturated alcohol can be obtained by one time distillation operation using a single distillation tower, and the purity of the γ,δ-unsaturated alcohol may be gradually increased by separating impurities stepwise by splitting the operation into two or more times through several distillation operations using two or more distillation towers.

The thus obtained γ,δ-unsaturated alcohol has a purity of 99 mass % or more, and as compared with the case of not going through the alkali cleaning step, the purity and yield are improved by 1 mass % or more, and in the preferred embodiment, by about 1.5 mass %.

EXAMPLES

The present invention is hereunder specifically described with reference to Examples, but it should be construed that the present invention is by no means limited by these Examples.

The gas chromatography analysis in each of the Examples was performed under the following conditions.

(Gas Chromatography Analysis Conditions)

Apparatus: GC-14A (manufactured by Shimadzu Corporation)

Column used: G-300 (inside diameter: 1.2 mm, length: 20 m, film thickness: 2 μm), manufactured by Chemicals Evaluation and Research Institute, Japan Analysis conditions: Inlet temperature: 220° C., detector temperature: 220° C.

Sample injection amount: 0.2 μL

Carrier gas: Helium (260 kPa) is passed at a rate of 10 mL/min.

Column temperature: 80° C.→Temperature rise at 5° C/min→Held at 210° C. for 4 minutes Detector: Flame ionization detector (FID)

Production Example 1

Into a stainless steel-made reaction tube having an inside diameter of 2 mm and a length of 3,180 mm (internal volume: 10 mL) and heated at 280° C., a mixed solution composed of 5.7 mass % of formaldehyde, 5.7 mass % of water, 74.5 mass % of isobutene, and 14.1 mass % of tert-butanol (organic solvent) was fed at a rate of 1 mL/min. Here, a molar ratio of isobutene to tert-butanol to formaldehyde in the mixed solution is 7/1/1. A residence time of the mixed solution is 10 minutes. An outlet of the reaction tube was connected to a cooling tube having an inside diameter of 2 mm and a length of 2,000 mm, an outlet pressure of the cooling tube was kept at 20 MPa, and a reaction liquid was allowed to flow out.

The resulting reaction liquid was subjected to gas chromatography analysis. The results are shown in Table 1.

TABLE 1

| | Conversion of formaldehyde (%)*3 | Selectivity (%)*1 | | |
|---|---|---|---|---|
| | | 3-Methyl-3-buten-1-ol | Formic acid | Formic acid ester*2 |
| Production Example 1 | 88.1 | 84.5 | 2.3 | 1.0 |

*1Based on formaldehyde consumed, mol %
*2Formic acid ester of 3-methyl-3-buten-1-ol
*3mol %

Example 1

To 100 g of the reaction liquid obtained in Production Example 1 (corresponding to 65.1 g of isobutene, 14.1 g of tert-butanol, 5.7 g of water, 0.7 g of formaldehyde, 12.2 g of 3-methyl-3-buten-1-ol, 0.2 g of formic acid, 0.2 g of the formic acid ester of 3-methyl-3-buten-1-ol, and 1.8 g of others), 12 mL of a 1 mol/L sodium hydroxide aqueous solution (corresponding to 12 mmol of sodium hydroxide) was added, followed by stirring at 70° C. for 5 minutes. The resulting aqueous solution had pH of 12.8.

As a result of performing the gas chromatography analysis regarding an organic layer (upper layer), all of the formic acid and the formic acid ester of 3-methyl-3-buten-1-ol did not remain in the organic layer.

According to comparison with Comparative Example 1 as described later, it may be conjectured that the formic acid ester of 3-methyl-3-buten-1-ol was entirely converted into a formate and moved into an aqueous layer (3-methyl-3-buten-1-ol formed at the same time remained in the organic layer, thereby contributing to an improvement in the yield).

Example 2

The operation and analysis were performed in the same manner as in Example 1, except for changing the temperature to 30° C. The resulting aqueous solution had pH of 12.8.

The formic acid did not remain in the organic layer, and a residual amount of the formic acid ester of 3-methyl-3-buten-1-ol in the organic layer was 12 mass % (corresponding to 0.024 g) of that before stirring.

Example 3

The operation and analysis were performed in the same manner as in Example 1, except for changing the amount of the sodium hydroxide aqueous solution used to 7 mL (corresponding to 7 mmol of sodium hydroxide) and also changing the temperature to 30° C. The resulting aqueous solution had pH of 12.8.

The formic acid did not remain in the organic layer, and a residual amount of the formic acid ester of 3-methyl-3-buten-1-ol in the organic layer was 40 mass % (corresponding to 0.08 g) of that before stirring.

Comparative Example 1

The operation and analysis were performed in the same manner as in Example 1, except for changing 10 mL of water in place of 12 mL of the sodium hydroxide aqueous solution. The resulting aqueous solution had pH of 2.5.

The formic acid in an amount of 42 mass % (corresponding to 0.084 g) remained in the organic layer, and the formic acid ester of 3-methyl-3-buten-1-ol in an amount of 100 mass % remained as it was in the organic layer.

From the results of the aforementioned Examples and Comparative Example, it is noted that by bringing the reaction liquid obtained in Production Example 1 into contact with the alkaline aqueous solution to regulate the pH falling within the aforementioned range, the formic acid was efficiently removed from the organic layer, and the formic acid ester of 3-methyl-3-buten-1-ol was greatly removed from the organic layer.

Example 4

The organic layer (upper layer) obtained in Example 1 was subjected to purification by distillation under conditions of the number of theoretical plate of 20, a reflux ratio of 1.0, a bath temperature of 140° C., and a pressure of 5.3 kPa. As a result, 3-methyl-3-buten-1-ol having a purity of 99.4 mass % was obtained in a distillation yield of 95.0%.

As a result of the gas chromatography analysis, it was confirmed that the formic acid of 3-methyl-3-buten-1-ol was not included at all. In addition, the formation of any high-boiling compound at the time of purification by distillation could not be confirmed.

Comparative Example 2

The purification by distillation was performed in the same manner as in Example 4, except for using the organic layer obtained in Comparative Example 1 in place of the organic layer obtained in Example 1. As a result, 3-methyl-3-buten-1-ol having a purity of 97.9 mass % was obtained in a distillation yield of 95.0%.

As a result of the gas chromatography analysis, it was confirmed that 1.6 mass % of the formic acid ester of 3-methyl-3-buten-1-ol and 0.1 mass % of formic acid were present as impurities. In order to obtain 3-methyl-3-buten-1-ol having a much higher purity by the removal of the formic acid ester of 3-methyl-3-buten-1-ol, only a distillate having a high purity of 3-methyl-3-buten-1-ol has to be obtained. In that case, the yield of 3-methyl-3-buten-1-ol will be sacrificed. In addition, the formation amount of a high-boiling compound that may be considered to have been formed at the time of purification by distillation was corresponding to 0.4 mass % of the amount of the liquid of the organic layer used.

INDUSTRIAL APPLICABILITY

The γ,δ-unsaturated alcohol obtained by the production method of the present invention can become a raw material or intermediate for various organic compounds, and in particular, 3-methyl-3-buten-1-ol is useful as a precursor of isoprene and moreover as a raw material or intermediate for drugs and perfumes.

The invention claimed is:
1. A method for producing a γ,δ-unsaturated alcohol of formula (II):

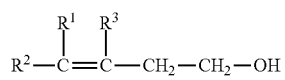

(II)

the method comprising:
reacting formaldehyde with an α-olefin of formula (I):

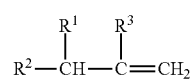

(I)

without a basic compound to obtain a reaction liquid, and
contacting the reaction liquid with an alkaline aqueous solution so as to obtain an aqueous solution having pH of 9 to 13 and to form an organic layer and an aqueous layer, wherein, in the formulae (I) and (II), $R^1$, $R^2$, and $R^3$ each independently represent a hydrogen atom, an optionally hydroxyl group-substituted alkyl group having 1 to 10 carbon atoms, an optionally hydroxyl group-substituted alkenyl group having 2 to 10 carbon atoms, or an optionally hydroxyl group-substituted aryl group having 6 to 12 carbon atoms, provided that $R^1$ and $R^3$ are optionally bonded to each other to form a ring.

2. The method according to claim 1, wherein an alkali in the alkaline aqueous solution is at least one selected from the group consisting of an alkali metal hydroxide, an alkali metal carbonate, an alkali metal acetate, an alkali metal phosphate, an alkaline earth metal hydroxide, an alkaline earth metal carbonate, an alkaline earth metal acetate, and an alkaline earth metal phosphate.

3. The method according to claim 2, wherein a concentration of the alkali in the alkaline aqueous solution is 0.01 to 20 mol/L.

4. The method according to claim 1, wherein said contacting is performed at a temperature of from 10 to 90° C.

5. The method according to claim 1, wherein said contacting is performed in a counter-current mode.

6. The method according to claim 1, further comprising: after said contacting, purifying the organic layer by distillation.

7. The method according to claim 1, wherein $R^3$ is an alkyl group having 1 to 5 carbon atoms.

8. The method according to claim 1, wherein at least one of $R^1$ and $R^2$ is a hydrogen atom.

9. The method according to claim 1, wherein said reacting is performed in the presence of a solvent in an amount of 0.5 to 20 mol per mol of formaldehyde.

10. The method according to claim 1, wherein formaldehyde in said reacting is dissolved in water.

11. The method according to claim 1, wherein said reacting is performed at a reaction temperature of from 150 to 350° C.

12. The method according to claim 11, wherein said reacting is performed at a reaction pressure that is set to a vapor pressure of the α-olefin at the reaction temperature or higher.

* * * * *